(12) United States Patent
Konno et al.

(10) Patent No.: US 9,200,023 B2
(45) Date of Patent: Dec. 1, 2015

US009200023B2

(54) METHOD FOR PRODUCING COMPLEX OF TRISORTHO-METALATED IRIDIUM, LIGHT-EMITTING MATERIAL USING SAID COMPLEX, AND LIGHT-EMITTING ELEMENT

(75) Inventors: Hideo Konno, Tsukuba (JP); Takashi Ito, Tokyo (JP); Yoshiro Sugita, Tokyo (JP)

(73) Assignee: National Institute of Advanced Industrial Science and Technology & Furuya Metal Co. Ltd., Tokyo (JP)

( * ) Notice: Subject to any disclaimer, the term of this patent is extended or adjusted under 35 U.S.C. 154(b) by 92 days.

(21) Appl. No.: 13/876,937

(22) PCT Filed: Oct. 25, 2011

(86) PCT No.: PCT/JP2011/074550
§ 371 (c)(1),
(2), (4) Date: Mar. 29, 2013

(87) PCT Pub. No.: WO2012/057138
PCT Pub. Date: May 3, 2012

(65) Prior Publication Data
US 2013/0203997 A1 Aug. 8, 2013

(30) Foreign Application Priority Data
Oct. 28, 2010 (JP) ................................ 2010-242751

(51) Int. Cl.
| | | |
|---|---|---|
| C07F 15/00 | (2006.01) | |
| C09K 11/06 | (2006.01) | |
| H01L 51/00 | (2006.01) | |
| H05B 33/14 | (2006.01) | |
| H01L 51/50 | (2006.01) | |

(52) U.S. Cl.
CPC ............ *C07F 15/0033* (2013.01); *C09K 11/06* (2013.01); *H01L 51/0085* (2013.01); *H05B 33/14* (2013.01); *C09K 2211/1007* (2013.01); *C09K 2211/1011* (2013.01); *C09K 2211/1029* (2013.01); *C09K 2211/1092* (2013.01); *C09K 2211/185* (2013.01); *H01L 51/5016* (2013.01)

(58) Field of Classification Search
USPC .................... 546/2, 10; 313/504; 428/690
See application file for complete search history.

(56) References Cited

U.S. PATENT DOCUMENTS

| | | | |
|---|---|---|---|
| 2005/0288507 | A1 | 12/2005 | Deaton |
| 2008/0131730 | A1 | 6/2008 | Takiguchi et al. |

FOREIGN PATENT DOCUMENTS

| | | |
|---|---|---|
| JP | 2002-105055 A | 10/2002 |
| JP | 2004-168756 A | 6/2004 |
| JP | 2007-070290 A | 3/2007 |
| JP | 2008-505076 A | 2/2008 |
| JP | 2010-189453 A | 9/2010 |
| WO | WO 02/44189 A1 | 6/2002 |

OTHER PUBLICATIONS

International Patentability Report on Patentability dated May 10, 2013 corresponding to Japanese Patent Application No. PCT/JP2011/074550.
Tamayo, et al., "Synthesis and Characterization of Facial and Meridional Tris-cyclometalated Iridium(III) Complexes", J. Am. Chem. Soc., 125, 2003, pp. 7377-7387.
International Search Report dated Dec. 13, 2011 for corresponding International Patent Application No. PCT/JP2011/074550 with English translation (3 pages).
German Office Action dated Jul. 28, 2015 corresponding to German Patent Application No. 11 2011 103 600.0; 10 pages.

*Primary Examiner* — Charanjit Aulakh
(74) *Attorney, Agent, or Firm* — Ohlandt Greeley Ruggiero & Perle L.L.P.

(57) ABSTRACT

A method for obtaining, with high selectivity as compared to a conventional method of mixing reaction substrates and thereafter reacting the mixture under heating, a facial isomer of tris-orthometallated iridium that is suitably used particularly as an organic electroluminescence device material, among complexes of tris-orthometallated iridium. The method for producing a complex of tris-orthometallated iridium according to the present disclosure includes, in order, a step (1) of preliminarily heating at least one of the complex of orthometallated iridium or the bidentate organic ligand; a step (2) of mixing the complex of orthometallated iridium and the bidentate organic ligand; and a step (3) of reacting the complex of orthometallated iridium and the bidentate organic ligand.

3 Claims, No Drawings

METHOD FOR PRODUCING COMPLEX OF TRISORTHO-METALATED IRIDIUM, LIGHT-EMITTING MATERIAL USING SAID COMPLEX, AND LIGHT-EMITTING ELEMENT

BACKGROUND

1. Field of the Disclosure

The present disclosure relates to a method for producing a complex of tris-orthometallated iridium that is suitably used as a material for an organic electroluminescence device, and particularly to a complex of tris-orthometallated iridium capable of increasing the production yield of a facial isomer of tris-orthometallated iridium which has high light emission efficiency and is excellent in thermal stability.

2. Discussion of the Background Art

Currently, organic electroluminescence devices receive attention as a next-generation display technique or lighting technique, and development of light emitting materials for organic electroluminescence devices are extensively conducted. Light emitting material can be classified into two types: fluorescence materials and phosphorescence materials, but attention is focused on phosphorescence materials which show higher light emission efficiency. Among them, complexes of tris-orthometallated iridium represented by tris(2-phenylpyridinato)iridium are a promising group of materials because they show high light emission efficiency and good thermal stability. So far, many production methods have been disclosed for obtaining such complexes of tris-orthometallated iridium (see, for example, Patent Documents 1 to 5).

Patent Document 1 discloses a method, wherein as shown in the reaction formula (chemical formula 1), a chlorine-bridged iridium dimer is synthesized from iridium trichloride n-hydrate, and used as a raw material to produce a complex of tris-orthometallated iridium.

[Chemical Formula 1]

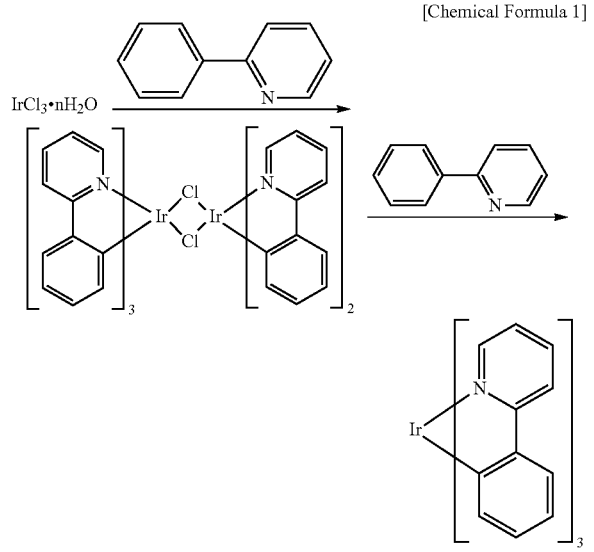

Patent Document 2 discloses a method, wherein as shown in the reaction formula (chemical formula 2), a chlorine-bridged iridium dimer is synthesized from iridium trichloride n-hydrate, and an iridium complex coordinated with acetylacetone is synthesized from the chlorine-bridged iridium dimer, and used as a raw material to produce a complex of tris-orthometallated iridium.

[Chemical Formula 2]

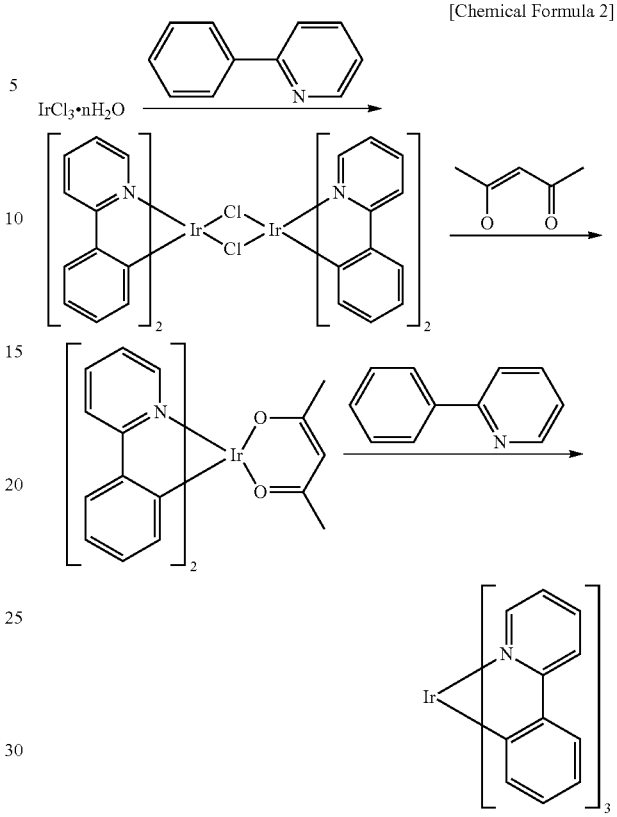

Patent Document 3 discloses a method, wherein as shown in the reaction formula (chemical formula 3), a chlorine-bridged iridium dimer is synthesized from iridium trichloride n-hydrate, and an iridium complex coordinated with acetonitrile is synthesized from the chlorine-bridged iridium dimer, and used as a raw material to produce a complex of tris-orthometallated iridium.

[Chemical Formula 3]

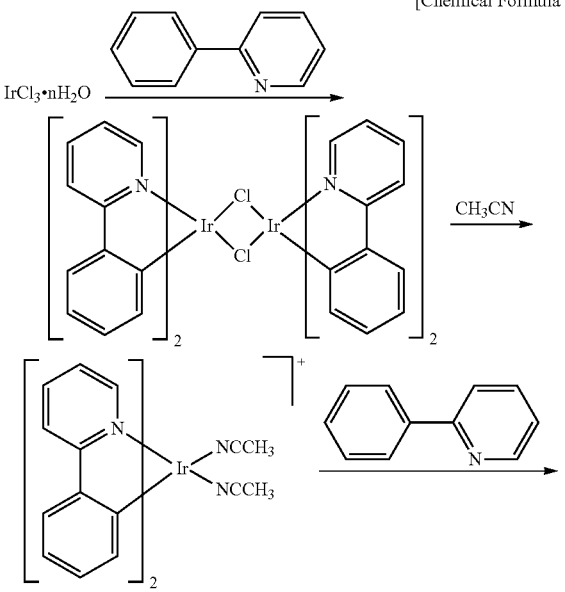

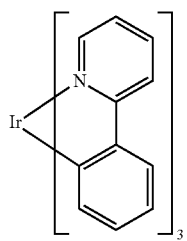

The production methods described in Patent Documents 1 to 3 are methods in which a complex of orthometallated iridium such as a chlorine-bridged iridium dimer is mixed with a bidentate organic ligand such as 2-phenylpyridinato, and the mixture is thereafter reacted under heating.

Patent Document 4 discloses a method, wherein glycerol as a reaction solvent is heated at 130° C. to 140° C. for 2 hours, and thereafter cooled to 100° C., 1-phenylisoquinoline and Ir(acac)$_3$ (acac: acetylacetone) are placed in the cooled glycerol, and the mixture is reacted under heating at around 210° C. for 7 hours to produce a complex of tris-orthometallated iridium. Patent Document 5 discloses a method, wherein a mixture of a bidentate organic ligand and glycerol is heated at 150° C. for about 60 minutes, and cooled, Ir(acac)$_3$ is thereafter added, and the mixture is heated to 200° C. to produce a complex of tris-orthometallated iridium.

PRIOR ART DOCUMENTS

Patent Documents

Patent Document 1: Japanese Patent Application Laid-Open (JP-A) No. 2004-168756
Patent Document 2: JP-A No. 2002-105055
Patent Document 3: Japanese Patent Application National Publication No. 2008-505076
Patent Document 4: International Publication No. 02/044189
Patent Document 5: JP-A No. 2010-189453

Non-Patent Document

Non-Patent Document 1: J. Am. Chem. Soc., 2003, Vol. 125, page 7377

SUMMARY OF DISCLOSURE

The production methods described in Patent Documents 1 to 3 are methods in which a complex of orthometallated iridium such as a chlorine-bridged iridium dimer is mixed with a bidentate organic ligand such as 2-phenylpyridinato, and the mixture is thereafter reacted under heating. In these methods, however, since a meridional isomer, a geometrical isomer, is generated as a by-product, it is not easy to obtain a facial isomer at a high purity. On the other hand, the production method described in Patent Document 4 is a method in which glycerol as a reaction solvent is heated beforehand and cooled, an iridium raw material and a bidentate organic ligand are thereafter added to the cooled glycerol, and the mixture is reacted under heating. The production method described in Patent Document 5 is a method in which glycerol containing a bidentate organic ligand is heated beforehand and cooled, an iridium raw material is thereafter added to the cooled glycerol, and the mixture is reacted under heating. The production methods described in Patent Documents 4 and 5 are similar to the method of the present disclosure, but the heating of glycerol as a reaction solvent, which is carried out beforehand, is intended for removing water contained in glycerol, and these production methods are different in the purpose of preliminary heating itself from the method of the present disclosure. With the available iridium raw material being limited to Ir(acac)$_3$, these methods may not be production methods of high generality, and the reaction thereof is completely different from that in the production method according to the present disclosure.

The complex of tris-orthometallated iridium has two geometrical isomers: facial isomer and meridional isomer, and it has been revealed that the facial isomer is superior in light emission efficiency and stability (see, for example, Non-Patent Document 1). However, it is difficult to conveniently separate geometrical isomers: facial isomer and meridional isomer, and for obtaining the facial isomer, it is necessary to carry out a post treatment of combining and repeating time-consuming operations such as recrystallization, column chromatography or sublimation refinement. The production methods described in the aforementioned Patent Documents 1 to 3 may not completely solve the problem that the meridional isomer as a geometrical isomer is generated as a by-product. Accordingly, as a method for producing a complex of tris-orthometallated iridium, a method for selectively producing the facial isomer by suppressing generation of the meridional isomer that is not desirable as an organic electroluminescence device material is eagerly desired.

The present disclosure has been devised in view of the circumstances of the aforementioned prior arts. It is an object of the present disclosure to provide a new production method for obtaining, with high selectivity as compared to a conventional method of mixing reaction substrates and thereafter reacting the mixture under heating, a facial isomer of tris-orthometallated iridium that is suitably used particularly as an organic electroluminescence device material, among complexes of tris-orthometallated iridium.

It is a second object of the present disclosure to provide a light-emitting material excellent in light emission efficiency and durability using a complex of tris-orthometallated iridium containing a facial isomer of tris-orthometallated iridium at a high ratio, and a light-emitting device using the light-emitting material.

For solving the aforementioned problems, the present inventors extensively conducted studies on a method for producing a complex of tris-orthometallated iridium. As a result, it has been found that surprisingly, the production yield of a facial isomer and a meridional isomer in the foregoing known production methods significantly depends on a method for adding a complex of orthometallated iridium as an iridium raw material and a bidentate organic ligand. That is, it has been revealed that by preliminarily heating at least one of two reaction substrates, i.e. an iridium raw material and a bidentate organic ligand, followed by mixing the iridium raw material and the bidentate organic ligand, and reacting the mixture, generation of the meridional isomer is suppressed, so that the purity of the facial isomer is significantly increased, as compared to a method of mixing two reaction substrates, and thereafter reacting the mixture under heating as in the production methods described in Patent Documents 1 to 3. So far, it has not been disclosed that the production yield of a facial isomer and a meridional isomer, geometrical isomers of a complex of tris-orthometallated iridium depends on a method for adding a complex of orthometallated iridium as an iridium raw material and a bidentate organic ligand, and this experimental fact is an important and new finding obtained through the accumulation of close experiments by the present inventors. Thus, the present inventors have succeeded in developing a method for producing, at a high purity as compared to the conventional production method, a facial isomer of tris-orthometallated iridium that is suitably used as an organic electroluminescence device material, thus leading to completion of the present disclosure.

As it has been revealed that the facial isomer of tris-orthometallated iridium is superior in light emission efficiency and stability to its geometrical isomer, i.e. the meridional isomer, it has been found that by using as a light-emitting material a complex of tris-orthometallated iridium produced by the present disclosure, a light-emitting device having high efficiency and high durability can be prepared, thus leading to completion of the present disclosure.

SUMMARY

A method for producing a complex of tris-orthometallated iridium according to the present disclosure is a method in which a complex of orthometallated iridium represented by general formula (chemical formula 4) and a bidentate organic ligand represented by general formula (chemical formula 5) are reacted as reaction substrates to produce a complex of tris-orthometallated iridium represented by general formula (chemical formula 6), wherein the method includes, in order, a step (1) of preliminarily heating at least one of the complex of orthometallated iridium or the bidentate organic ligand; a step (2) of mixing the complex of orthometallated iridium and the bidentate organic ligand; and a step (3) of reacting the complex of orthometallated iridium and the bidentate organic ligand.

[Chemical Formula 4]

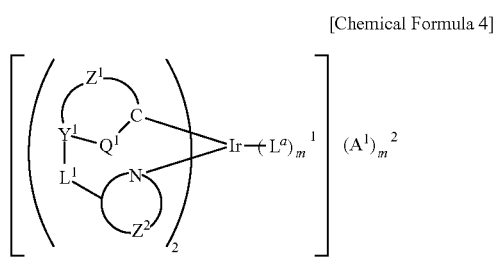

(In general formula (chemical formula 4), $L^a$ represents a ligand. $A^1$ represents a counter anion. $m^1$ represents 1 or 2. $m^2$ represents 0 or 1. $Z^1$ and $Z^2$ each independently represent a group of non-metal atoms required for forming a five-membered ring or six-membered ring. Further, the ring formed may form a fused ring with still another ring. $L^1$ represents a single bond or a divalent group. $Y^1$ represents a nitrogen atom or a carbon atom. When $Y^1$ is a nitrogen atom, $Q^1$ indicates that a carbon atom and $Y^1$ are bonded to each other by a single bond. When $Y^1$ is a carbon atom, $Q^1$ indicates that a carbon atom and $Y^1$ are bonded to each other by a double bond.)

[Chemical Formula 5]

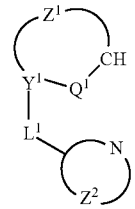

(In general formula (chemical formula 5), $Z^1$, $Z^2$, $Y^1$, $Q^1$ and $L^1$ each have the same meaning as in general formula (chemical formula 4).)

[Chemical Formula 6]

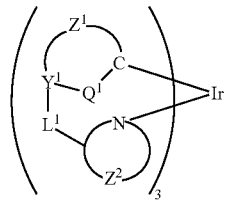

(In general formula (chemical formula 6), $Z^1$, $Z^2$, $Y^1$, $Q^1$ and $L^1$ each have the same meaning as in general formula (chemical formula 4).)

In the method for producing a complex of tris-orthometallated iridium according to the present disclosure, the step (1) is preferably a step of preliminarily heating one of the complex of orthometallated iridium and the bidentate organic ligand. The reaction can be carried out more efficiently.

The method for producing a complex of tris-orthometallated iridium according to the present disclosure encompasses such a form that the complex of orthometallated iridium is a compound represented by general formula (chemical formula 7).

[Chemical Formula 7]

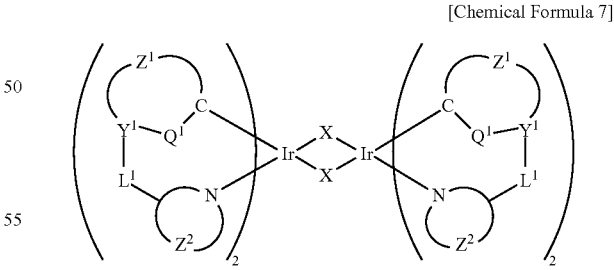

(In general formula (chemical formula 7), X represents a halogen atom. $Z^1$, $Z^2$, $Y^1$, $Q^1$ and $L^1$ each have the same meaning as in general formula (chemical formula 4).)

The method for producing a complex of tris-orthometallated iridium according to the present disclosure encompasses such a form that the $L^a$ is a monoanionic ligand.

The method for producing a complex of tris-orthometallated iridium according to the present disclosure encompasses such a form that the $L^a$ is a neutral ligand.

The method for producing a complex of tris-orthometallated iridium according to the present disclosure encompasses such a form that the complex of orthometallated iridium is a compound represented by general formula (chemical formula 8).

[Chemical Formula 8]

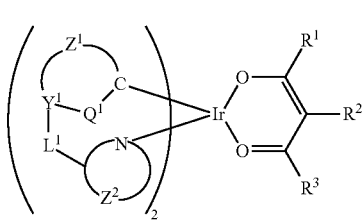

(In general formula (chemical formula 8), $R^1$ to $R^3$ each represent a hydrogen atom, a deuterium atom or a substituent. $Z^1$, $Z^2$, $Y^1$, $Q^1$ and $L^1$ each have the same meaning as in general formula (chemical formula 4).)

The method for producing a complex of tris-orthometallated iridium according to the present disclosure encompasses such a form that the complex of orthometallated iridium is a compound represented by general formula (chemical formula 9).

[Chemical Formula 9]

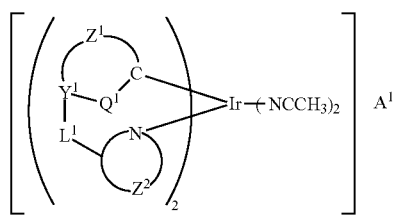

(In general formula (chemical formula 9), $A^1$, $Z^1$, $Z^2$, $Y^1$, $Q^1$ and $L^1$ each have the same meaning as in general formula (chemical formula 4).)

The method for producing a complex of tris-orthometallated iridium according to the present disclosure encompasses such a form that the bidentate organic ligand is at least one selected from compounds (7) to (17) shown in general formula (chemical formula 10).

[Chemical Formula 10]

(7)

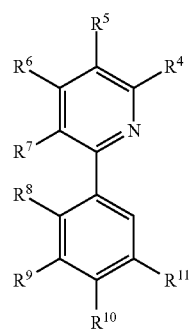

-continued (8)

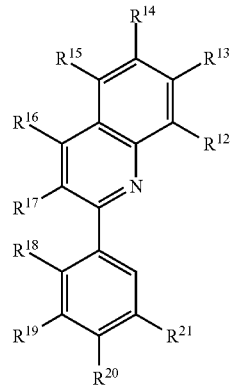

(9)

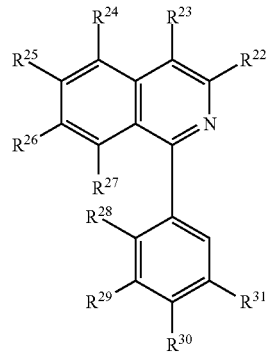

(10)

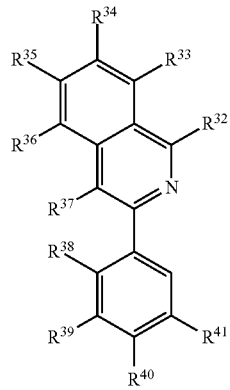

(11)

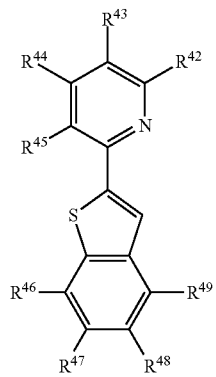

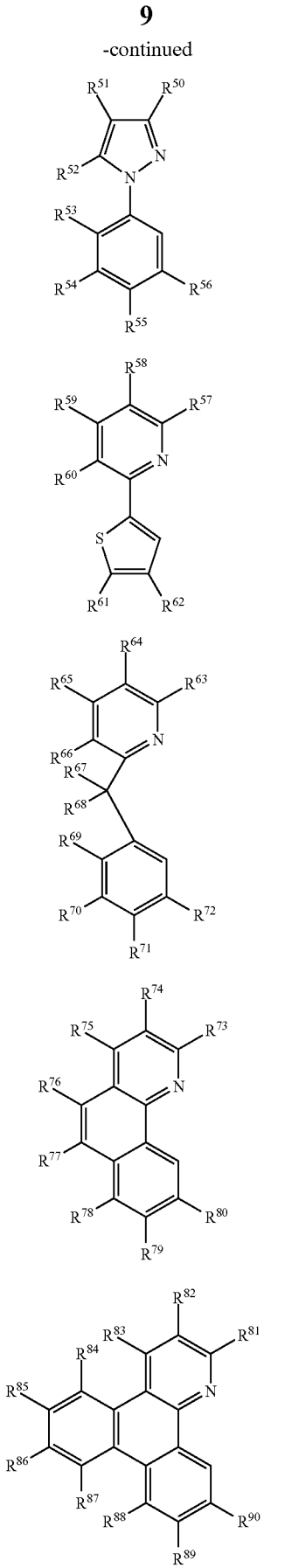

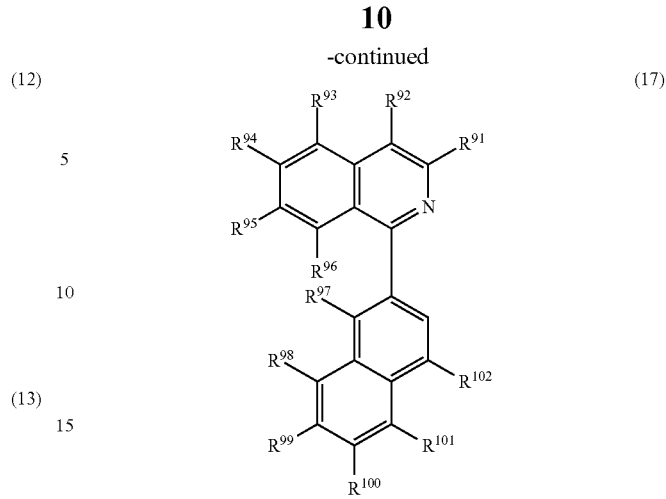

(In (7) to (17) shown in general formula (chemical formula 10), $R^4$ to $R^{102}$ each represent a hydrogen atom, a deuterium atom or a substituent.)

In the method for producing a complex of tris-orthometallated iridium according to the present disclosure, the reaction temperature in the step (3) is preferably in a range of 100 to 300° C. The production yield of the facial isomer can be further increased.

In the method for producing a complex of tris-orthometallated iridium according to the present disclosure, the preliminary heating temperature in the step (1) is preferably equal to or lower than the reaction temperature in the step (3) and in a range of 100 to 300° C. The production yield of the facial isomer can be further increased.

In the method for producing a complex of tris-orthometallated iridium according to the present disclosure, the step (1) is preferably a step of preliminarily heating the bidentate organic ligand.

In the method for producing a complex of tris-orthometallated iridium according to the present disclosure, the step (3) is preferably carried out under irradiation of a microwave. Since the temperature can be elevated in a short time, the production yield of the facial isomer can be further increased.

A light-emitting material according to the present disclosure includes the complex of tris-orthometallated iridium produced by the production method according to the present disclosure.

A light-emitting device according to the present disclosure uses the light-emitting material according to the present disclosure.

Effects of the Disclosure

The present disclosure can provide a new production method for obtaining, with high selectivity as compared to a conventional method of mixing reaction substrates and thereafter reacting the mixture under heating, a facial isomer of tris-orthometallated iridium that is suitably used particularly as an organic electroluminescence device material, among complexes of tris-orthometallated iridium. The present disclosure can also provide a light-emitting material excellent in light emission efficiency and durability using a complex of tris-orthometallated iridium containing a facial isomer of tris-orthometallated iridium at a high ratio, and a light-emitting device using the light-emitting material.

DETAILED DESCRIPTION OF THE PREFERRED EMBODIMENT

Next, the present disclosure will be described in detail by referring to an embodiment, but the present disclosure is not construed as being limited to the descriptions thereof. The embodiment may be modified in a variety of ways as long as the effect of the present disclosure is exhibited.

Symbols (($Z^1$, $Z^2$, $Y^1$, $Q^1$, $L^1$, $L^a$, $m^1$, $m^2$, $A^1$, X and $R^1$ to $R^{102}$) described in general formulae (chemical formula 4) to (chemical formula 9) and (7) to (17) of (chemical formula 10) in this specification will be explained in detail below.

$Z^1$ and $Z^2$ each independently represent a group of nonmetal atoms required for forming a five-membered ring or six-membered ring. The ring formed may have a substituent, or may form a fused ring with still another ring. The substituent is, for example, a halogen atom, an alkyl group, a substituted alkyl group, a phenoxy group, a substituted phenoxy group, an aryl group, a substituted aryl group, an alkoxy group, a substituted alkoxy group, a dialkylamino group or a substituted dialkylamino group. Preferable is a halogen atom, an alkyl group having 1 to 30 carbon atoms, a substituted alkyl group having 1 to 30 carbon atoms, a phenoxy group having 6 to 30 carbon atoms, a substituted phenoxy group having 6 to 30 carbon atoms, an aryl group having 6 to 30 carbon atoms, a substituted aryl group having 6 to 30 carbon atoms, an alkoxy group having 1 to 30 carbon atoms, a substituted alkoxy group having 1 to 30 carbon atoms, a dialkylamino group having 2 to 30 carbon atoms or a substituted dialkylamino group having 2 to 30 carbon atoms. More preferable is a halogen atom, an alkyl group having 1 to 10 carbon atoms, a substituted alkyl group having 1 to 10 carbon atoms, an aryl group having 6 to 10 carbon atoms, a substituted aryl group having 6 to 10 carbon atoms, an alkoxy group having 1 to 10 carbon atoms or a substituted alkoxy group having 1 to 10 carbon atoms. Especially preferable is a halogen atom, an alkyl group having 1 to 4 carbon atoms or a substituted alkyl group having 1 to 4 carbon atoms.

The five-membered ring or six-membered ring formed by $Z^1$ is preferably an aromatic ring or a heteroaromatic ring, more preferably an aromatic ring. The five-membered ring or six-membered ring formed by $Z^1$ is, for example, a quinoline ring, a benzoquinoline ring, a quinoxaline ring, an isoquinoline ring, a phenanthridine ring, a phenazine ring, an acridine ring, a triazole ring, an imidazophenanthridine ring, a phthalazine ring, a quinazoline ring, a naphthyridine ring, a cinnoline ring, a perimidine ring, a phenanthroline ring, a benzimidazole ring, a benzoxazole ring, a benzthiazole ring, an imidazole ring, a thiazole ring, an oxazole ring, a pyrrole ring, an oxadiazole ring, a thiadiazole ring, a pyrazole ring, a 1,2,3-triazole ring, a 1,2,4-triazole ring, a pyridine ring, a pyrimidine ring, a pyrazine ring, a pyridazine ring, a furan ring, a thiophene ring, a naphthalene ring, a fluorene ring, a dibenzothiophene ring, a dibenzofuran ring, a carbazole ring or a benzene ring. Among them, a pyrrole ring, a pyridine ring, a naphthalene ring, a fluorene ring, a dibenzothiophene ring, a dibenzofuran ring, a carbazole ring or a benzene ring is preferable. A naphthalene ring, a fluorene ring, a dibenzothiophene ring, a dibenzofuran ring, a carbazole ring or a benzene ring is more preferable, and a benzene ring is especially preferable.

The five-membered ring or six-membered ring formed by $Z^2$ is preferably a heteroaromatic ring. The five-membered ring or six-membered ring formed by $Z^2$ is, for example, an imidazole ring, a thiazole ring, an oxazole ring, a pyrrole ring, an oxadiazole ring, a thiadiazole ring, a pyrazole ring, a 1,2,3-triazole ring, a 1,2,4-triazole ring, a selenazole ring, a pyridine ring, a pyrimidine ring, a pyrazine ring or a pyridazine ring. Among them, an imidazole ring, a thiazole ring, a 1,2,3-triazole ring, a 1,2,4-triazole ring, an oxazole ring, a pyrrole ring, a pyrazole ring, a pyridine ring or a pyrimidine ring is preferable, and a pyrazole ring or a pyridine ring is further preferable.

$L^1$ represents a single bond or a divalent group. The divalent group is, for example, —C(R)(R')—, —N(R)—, —O—, —P(R)— or —S—. Here, R and R' each represent a hydrogen atom or a substituent. The substituent is, for example, a halogen atom, an aliphatic group, an aromatic group, a heterocyclic group, a cyano group or a nitro group. $L^1$ is preferably a single bond, or —C(R)(R')— where R and R' each are a hydrogen atom, an aliphatic group or an aromatic group. $L^1$ is especially preferably a single bond.

$Y^1$ represents a nitrogen atom or a carbon atom. When $Y^1$ is a nitrogen atom, $Q^1$ indicates that the bond between a carbon atom and $Y^1$ is a single bond. When $Y^1$ is a carbon atom, $Q^1$ indicates that the bond between a carbon atom and $Y^1$ is a double bond.

$Q^1$ represents a bond between atoms. When $Y^1$ is a nitrogen atom, $Q^1$ indicates that a carbon atom and $Y^1$ are bonded to each other by a single bond. When $Y^1$ is a carbon atom, $Q^1$ indicates that a carbon atom and $Y^1$ are bonded to each other by a double bond.

As long as $L^a$ is a ligand, it may be a monodentate ligand or a bidentate ligand. $L^a$ may contain a metal (for example iridium), and may form so called a dinuclear complex.

$L^a$ is preferably an anionic ligand or a neutral ligand. $L^a$ is especially preferably a monoanionic ligand or a neutral ligand.

Next, a preferred structure of $L^a$ will be shown specifically. The monodentate anionic ligand is, for example, a halogen ligand, a hydroxy ligand, an alkoxide ligand, a phenoxide ligand, a thiocyanate ligand, a cyanate ligand or an isocyanate ligand. The bidentate anionic ligand is, for example, a β-diketonate ligand, an acetylacetonate ligand, an acetate ligand or a picolinate ligand.

The monodentate neutral ligand is a nitrile ligand (for example, acetonitrile ligand or propionitrile ligand), a sulfoxide ligand (for example, dimethylsulfoxide ligand), an amide ligand (for example, dimethylformamide ligand), an ether ligand (for example, tetrahydrofuran ligand), a water ligand, an ammonia ligand, an amine ligand, a piperidine ligand, a pyridine ligand or a pyrazine ligand. The bidentate neutral ligand is, for example, a bipyridine ligand, a phenanthroline ligand, a dipyridylamine ligand or an ethylenediamine ligand.

$m^1$ represents 1 or 2. Preferably $m^1=2$ when $L^a$ is a monodentate ligand, and preferably $m^1=1$ when $L^a$ is a bidentate ligand.

$m^2$ represents 0 or 1. Preferably $m^2=1$ when $L^a$ is a monodentate monoanionic ligand, preferably $m^2=0$ when $L^a$ is a bidentate monoanionic ligand, and preferably $m^2=1$ when $L^a$ is a neutral ligand.

$A^1$ represents a counter anion. The counter anion is not particularly limited as long as it is anionic, but a counter monoanion is preferable. The counter anion is, for example, $F^-$, $Cl^-$, $Br^-$, $I^-$, $BF_4^-$, $PF_6^-$, $ClO_4^-$, $CF_3CF_2CF_2COO^-$, $CF_3SO_3^-$, $CF_3CO_2^-$, $CH_3CO_2^-$, $SCN^-$, $CH_3SO_3^-$ or $SbF_6^-$. Among them preferable is $Cl^-$, $PF_6^-$, $BF_4^-$ or $CF_3SO_3^-$.

X represents a halogen atom. Preferable is a chlorine atom or a bromine atom, further preferable is a chlorine atom.

$R^1$ to $R^{102}$ each represent a hydrogen atom, a deuterium atom or a substituent. The substituent is, for example, an alkyl group (the alkyl group has preferably 1 to 30 carbon atoms, more preferably 1 to 20 carbon atoms, especially preferably 1 to 10 carbon atoms, with examples thereof including methyl, ethyl, iso-propyl, tert-butyl, n-octyl, n-decyl, n-hexadecyl, cyclopropyl, cyclopentyl and cyclohexyl), an alkenyl group (the alkenyl group has preferably 2 to 30 carbon atoms, more preferably 2 to 20 carbon atoms, especially preferably 2 to 10 carbon atoms, with examples thereof including vinyl, allyl, 2-butenyl and 3-pentenyl), an alkynyl group (the alkynyl group has preferably 2 to 30 carbon atoms, more preferably 2 to 20 carbon atoms, especially preferably 2 to 10 carbon atoms, with examples thereof including propargyl and 3-pentynyl), an aryl group (the aryl group has preferably 6 to 30 carbon atoms, more preferably 6 to 20 carbon atoms, especially preferably 6 to 12 carbon atoms, with examples thereof including phenyl, p-methylphenyl, naphthyl and anthranil), an amino group (the amino group has preferably 0 to 30 carbon atoms, more preferably 0 to 20 carbon atoms, especially preferably 0 to 10 carbon atoms, with examples thereof including amino, methylamino, dimethylamino, diethylamino, dibenzylamino, diphenylamino and ditolylamino), an alkoxy group (the alkoxy group has preferably 1 to 30 carbon atoms, more preferably 1 to 20 carbon atoms, especially preferably 1 to 10 carbon atoms, with examples thereof including methoxy, ethoxy, butoxy and 2-ethylhexyloxy), an aryloxy group (the aryloxy group has preferably 6 to 30 carbon atoms, more preferably 6 to 20 carbon atoms, especially preferably 6 to 12 carbon atoms, with examples thereof including phenyloxy, 1-naphthyloxy and 2-naphthyloxy), heterocyclic-oxy group (the heterocyclic-oxy group has preferably 1 to 30 carbon atoms, more preferably 1 to 20 carbon atoms, especially preferably 1 to 12 carbon atoms, with examples thereof including pyridyloxy, pyrazyloxy, pyrimidyloxy and quinolyloxy), an acyl group (the acyl group has preferably 1 to 30 carbon atoms, more preferably 1 to 20 carbon atoms, especially preferably 1 to 12 carbon atoms, with examples thereof including acetyl, benzoyl, formyl and pivaloyl), an alkoxycarbonyl group (the alkoxycarbonyl group has preferably 2 to 30 carbon atoms, more preferably 2 to 20 carbon atoms, especially preferably 2 to 12 carbon atoms, with examples thereof including methoxycarbonyl and ethoxycarbonyl), an aryloxycarbonyl group (the aryloxycarbonyl group has preferably 7 to 30 carbon atoms, more preferably 7 to 20 carbon atoms, especially preferably 7 to 12 carbon atoms, with examples thereof including phenyloxycarbonyl), an acyloxy group (the acyloxy group has preferably 2 to 30 carbon atoms, more preferably 2 to 20 carbon atoms, especially preferably 2 to 10 carbon atoms, with examples thereof including acetoxy and benzoyloxy), an acylamino group (the acylamino group has preferably 2 to 30 carbon atoms, more preferably 2 to 20 carbon atoms, especially preferably 2 to 10 carbon atoms, with examples thereof including acetylamino and benzoylamino), an alkoxycarbonylamino group (the alkoxycarbonylamino group has preferably 2 to 30 carbon atoms, more preferably 2 to 20 carbon atoms, especially preferably 2 to 12 carbon atoms, with examples thereof including methoxycarbonylamino), an aryloxycarbonylamino group (the aryloxycarbonylamino group has preferably 7 to 30 carbon atoms, more preferably 7 to 20 carbon atoms, especially preferably 7 to 12 carbon atoms, with examples thereof including phenyloxycarbonylamino), a sulfonylamino group (the sulfonylamino group has preferably 1 to 30 carbon atoms, more preferably 1 to 20 carbon atoms, especially preferably 1 to 12 carbon atoms, with examples thereof including methanesulfonylamino and benzenesulfonylamino), a sulfamoyl group (the sulfamoyl group has preferably 0 to 30 carbon atoms, more preferably 0 to 20 carbon atoms, especially preferably 0 to 12 carbon atoms, with examples thereof including sulfamoyl, methylsulfamoyl, dimethylsulfamoyl and phenylsulfamoyl), a carbamoyl group (the carbamoyl group has preferably 1 to 30 carbon atoms, more preferably 1 to 20 carbon atoms, especially preferably 1 to 12 carbon atoms, with examples thereof including carbamoyl, methylcarbamoyl, diethylcarbamoyl and phenylcarbamoyl), an alkylthio group (the alkylthio group has preferably 1 to 30 carbon atoms, more preferably 1 to 20 carbon atoms, especially preferably 1 to 12 carbon atoms, with examples thereof including methylthio and ethylthio), an arylthio group (the arylthio group has preferably 6 to 30 carbon atoms, more preferably 6 to 20 carbon atoms, especially preferably 6 to 12 carbon atoms, with examples thereof including phenylthio), a heterocyclic-thio group (the heterocyclic-thio group has preferably 1 to 30 carbon atoms, more preferably 1 to 20 carbon atoms, especially preferably 1 to 12 carbon atoms, with examples thereof including pyridylthio, 2-benzimidazolylthio, 2-benzoxazolylthio and 2-benzthiazolylthio), a sulfonyl group (the sulfonyl group has preferably 1 to 30 carbon atoms, more preferably 1 to 20 carbon atoms, especially preferably 1 to 12 carbon atoms, with examples thereof including mesyl and tosyl), a sulfinyl group (the sulfinyl group has preferably 1 to 30 carbon atoms, more preferably 1 to 20 carbon atoms, especially preferably 1 to 12 carbon atoms, with examples thereof including methanesulfinyl and benzenesulfinyl), an ureide group (the ureide group has preferably 1 to 30 carbon atoms, more preferably 1 to 20 carbon atoms, especially preferably 1 to 12 carbon atoms, with examples thereof including ureide, methylureide and phenylureide), a phosphoric amide group (the phosphoric amide group has preferably 1 to 30 carbon atoms, more preferably 1 to 20 carbon atoms, especially preferably 1 to 12 carbon atoms, with examples thereof including diethyl phosphoric amide and phenyl phosphoric amide), a hydroxy group, a mercapto group, a halogen atom (examples thereof include a fluorine atom, a chlorine atom, a bromine atom and an iodine group), a cyano group, a sulfo group, a carboxyl group, a nitro group, a trifluoromethyl group, a hydroxamic acid group, a sulfino group, a hydrazino group, an imino group, a heterocyclic-group (the heterocyclic group has preferably 1 to 30 carbon atoms, more preferably 1 to 12 carbon atoms, and has, for example, a nitrogen atom, an oxygen atom or a sulfur atom as a heteroatom, with examples thereof including imidazolyl, pyridyl, quinolyl, furyl, thienyl, piperidyl, morpholino, benzoxazolyl, benzimidazolyl, benzthiazolyl, carbazolyl group and an azepinyl group), a silyl group (the silyl group has preferably 3 to 40 carbon atoms, more preferably 3 to 30 carbon atoms, especially preferably 3 to 24 carbon atoms, with examples thereof including trimethylsilyl and triphenylsilyl), or a silyloxy group (the silyloxy group has preferably 3 to 40 carbon atoms, more preferably 3 to 30 carbon atoms, especially preferably 3 to 24 carbon atoms, with examples thereof including trimethylsilyloxy and triphenylsilyloxy). The preferred substituent is a cyano group, a trifluoromethyl group, a halogen atom, an alkyl group, an alkoxy group, an aryl group, an amino group or a heterocyclic-group.

$R^1$ and $R^3$ are more preferably an alkyl group having 1 to 10 carbon atoms, especially preferably an alkyl group having 1 to 5 carbon atoms, among those shown above as an example as $R^1$ to $R^{102}$. The alkyl group is, for example, methyl, ethyl, iso-propyl or tert-butyl. Among them, methyl and tert-butyl are more preferable, and methyl is most preferable.

$R^2$ is more preferably a hydrogen atom, a deuterium atom or an alkyl group having 1 to 10 carbon atoms, especially preferably a hydrogen atom or an alkyl group having 1 to 5 carbon atoms, most preferably a hydrogen atom, among those shown above as an example as $R^1$ to $R^{102}$.

$R^4$ to $R^{102}$ are more preferably a hydrogen atom, a deuterium atom, a cyano group, a trifluoromethyl group, a fluorine atom, an alkyl group having 1 to 30 carbon atoms, an alkoxy group having 1 to 30 carbon atoms, an aryl group having 6 to 30 carbon atoms, or an amino group having 0 to 30 carbon atoms, especially preferably a hydrogen atom, a fluorine atom, an alkyl group having 1 to 20 carbon atoms, an aryl group having 6 to 20 carbon atoms, or an amino group having 0 to 20 carbon atoms, among those shown above as an example as $R^1$ to $R^{102}$.

A method for producing a complex of tris-orthometallated iridium according to this embodiment is a method in which a complex of orthometallated iridium represented by general formula (chemical formula 4) and a bidentate organic ligand represented by general formula (chemical formula 5) are reacted as reaction substrates to produce a complex of tris-orthometallated iridium represented by general formula (chemical formula 6), wherein the method includes, in order, a step (1) of preliminarily heating at least one of the complex of orthometallated iridium or the bidentate organic ligand; a step (2) of mixing the complex of orthometallated iridium and the bidentate organic ligand; and a step (3) of reacting the complex of orthometallated iridium and the bidentate organic ligand.

The complex of orthometallated iridium represented by general formula (chemical formula 4) is preferably a compound represented by general formula (chemical formula 7), a compound represented by general formula (chemical formula 8) or a compound represented by general formula (chemical formula 9).

The compound represented by general formula (chemical formula 7) is an iridium binuclear complex in which a halogen ligand is coordinated as $L^a$. The halogen ligand is, for example, chlorine, bromine, iodine or fluorine. Among them, a structure in which chlorine is coordinated (hereinafter, referred to as chlorine-bridged iridium dimer in some cases) is especially preferable. The compound represented by general formula (chemical formula 8) is a complex of orthometallated iridium in which a β-diketonate ligand is coordinated as $L^a$. The compound represented by general formula (chemical formula 9) is a complex of orthometallated iridium in which an acetonitrile ligand is coordinated as $L^a$.

The bidentate organic ligand represented by general formula (chemical formula 5) is a bidentate organic ligand which can form an iridium-nitrogen bond or an iridium-carbon bond. The bidentate organic ligand is preferably at least one selected from compounds (7) to (17) shown in general formula (chemical formula 10). A bidentate organic ligand represented by (7), (8), (9) or (15) shown in general formula (chemical formula 10) is more preferable, a bidentate organic ligand represented by (7), (9) or (15) shown in general formula (chemical formula 10) is especially preferable, and a bidentate organic ligand represented by (7) or (15) shown in general formula (chemical formula 10) is particularly preferable. Other examples of the bidentate organic ligand may include bidentate organic ligands described in International Publication No. 01/041512, International Publication No. 02/15645 and JP-A No. 2001-247859.

In the present disclosure, heating means for elevating the temperature to a predetermined reaction temperature in the step (3) is not particularly limited, and either a conventional external heating system such as an oil bath, a mantle heater, a block heater or a heat medium circulating jacket, or a microwave irradiation system can be applied. However, for obtaining a higher facial isomer selectivity in a shorter time, the microwave irradiation system is preferably selected.

The frequency of the microwave is not particularly limited, but is preferably 300 MHz to 300 GHz, more preferably 500 MHz to 10000 MHz, especially preferably 2000 MHz to 3000 MHz, particularly preferably 2400 MHz to 2500 MHz.

The reaction time for heating by the microwave irradiation system depends on the output of a microwave reaction apparatus, the organic ligand, the type of a solvent used, and the liquid amount, but is preferably 1 minute to 180 minutes, more preferably 3 minutes to 120 minutes, especially preferably 5 minutes to 90 minutes, particularly preferably 10 minutes to 60 minutes.

The microwave is preferably continuously applied at a predetermined constant output without varying (reducing) the output even when a predetermined reaction temperature is reached. The output of the microwave is preferably 1 W to 15 kW. It is more preferably 100 W to 10 kW, especially preferably 500 W to 8 kW, particularly preferably 1 kW to 6 kW.

In the case of external heating by an oil bath, a mantle heater or the like, on the other hand, the reaction time depends on the organic ligand, the type of a solvent used and the liquid amount, but is preferably 10 minutes to 96 hours, more preferably 1 hour to 72 hours, especially preferably 1 hour to 48 hours, particularly preferably 1 hour to 24 hours.

In this embodiment, a reaction solvent is preferably used for ensuring that the reaction proceeds smoothly. The reaction solvent is not particularly limited, but an alcohol-based solvent, a protic solvent, an aprotic solvent, a hydrocarbon-based solvent, a nitrile-based solvent, an ionic solvent or the like is suitably used. The boiling point of a reaction solvent used is preferably 100° C. to 300° C., more preferably 150° C. to 285° C., especially preferably 160° C. to 250° C., particularly preferably 180° C. to 230° C. Examples of the reaction solvent include 2-ethoxyethanol, DMF (N,N-dimethylformamide), diglyme, dodecane, ethylene glycol, 1,2-propanediol, 1,3-propanediol, 1,3-butanediol and glycerol. Among them, 2-ethoxyethanol, DMF, diglyme, dodecane, ethylene glycol, 1,2-propanediol, 1,3-propanediol and 1,3-butanediol are preferable, and diols such as ethylene glycol, 1,2-propanediol, 1,3-propanediol and 1,3-butanediol are especially preferable. These reaction solvents can be used alone or as a mixed solvent including two or more kinds.

In this embodiment, at least one of two reaction substrates: a complex of orthometallated iridium represented by general formula (chemical formula 4) and a bidentate organic ligand represented by general formula (chemical formula 5) is preliminarily heated, and at this time, at least one reaction substrate may uniformly dissolved or uniformly dispersed in a dispersion medium beforehand. As the dispersion medium, one or more of those shown as an example in the aforementioned reaction solvents may be mixed and used, but one homogeneous to the reaction solvent is preferably selected. In the method for producing a complex of tris-orthometallated iridium according to this embodiment, the step (1) is preferably a step of preliminarily heating one of the complex of orthometallated iridium and the bidentate organic ligand. Particularly, the reaction substrate that is preliminarily heated is preferably a bidentate organic ligand represented by general formula (chemical formula 5). Therefore, especially preferably a bidentate organic ligand represented by general formula (chemical formula 5) or a reaction solution containing a bidentate organic ligand represented by general formula (chemical formula 5) is preliminarily heated, and thereto is added a complex of orthometallated iridium represented by general formula (chemical formula 4) or a reaction solution containing a complex of orthometallated iridium represented by general formula (chemical formula 4), and the mixture is reacted under heating. When only one of the reaction substrates is preliminarily heated, preferably the reaction substrate which is not preliminarily heated is added as a powder, or the amount of dispersion medium dissolving or dispersing the reaction substrate, which is not preliminarily heated, is minimized. Consequently, a decrease in the temperature of the preliminarily heated reaction solution can be suppressed.

In the production method according to this embodiment, steps (1) to (3) are carried out preferably under an inert gas atmosphere, especially preferably under a nitrogen atmosphere or an argon atmosphere.

In the method for producing a complex of tris-orthometallated iridium according to this embodiment, the reaction temperature in the step (3) is preferably in a range of 100° C. to 300° C. The reaction temperature is more preferably in a range of 155° C. to 300° C., especially preferably 155° C. to 285° C., further especially preferably 160° C. to 250° C., particularly preferably 180° C. to 230° C. If the reaction temperature is lower than 100° C., the production yield of the meridional isomer may be increased. If the reaction temperature is higher than 300° C., a decomposition reaction may easily proceed to reduce the yield.

In the method for producing a complex of tris-orthometallated iridium according to this embodiment, preferably the preliminary heating temperature in the step (1) is equal to or lower than the reaction temperature in the step (3) and a difference between the preliminary heating temperature and the reaction temperature is small. The difference between the preliminary heating temperature and the reaction temperature is preferably 100° C. or lower, more preferably 50° C. or lower, especially preferably 20° C. or lower, particularly preferably 10° C. or lower. If the difference in temperature is higher than 100° C., it may take a long time to reach the reaction temperature, and the production yield of the meridional isomer may be increased, leading to a reduction in the production yield of the facial isomer.

In the method for producing a complex of tris-orthometallated iridium according to this embodiment, the preliminary heating temperature in the step (1) is preferably equal to or lower than the reaction temperature in the step (3) and in a range of 100° C. to 300° C. The preliminary heating temperature is more preferably in a range of 155° C. to 300° C., especially preferably 155° C. to 285° C., further especially preferably 160° C. to 250° C., particularly preferably 180° C. to 230° C. If the preliminary heating temperature is lower than 100° C., the production yield of the meridional isomer may be increased. If the preliminary heating temperature is higher than 300° C., a decomposition reaction may easily proceed to reduce the yield.

In the production method according to this embodiment, the preliminary heating temperature is preferably less than 60 minutes, more preferably less than 30 minutes, especially preferably less than 15 minutes, further especially preferably less than 5 minutes after a desired temperature is reached. In this embodiment, preliminary heating is not intended for removing water in, for example, a reaction solvent, but is a preparation step for the step (2), and therefore it is preferable to proceed to the next step (2) immediately when a desired temperature is reached.

After performing preliminary heating in the step (1), subsequent steps (2) and (3) are preferably carried out without undergoing a cooling step. Here, cooling does not include a temporary temperature decrease, such as a temperature decrease resulting from interruption of irradiation of a microwave between the step (1) and the step (2) or a temperature decrease resulting from addition of a chemical. That is, the cooling step in this specification refers to a step of intentionally causing a temperature decrease by standing or cooling down a subject until a predetermined temperature is reached. Thus, for example, the temperature fall is preferably less than 30° C., more preferably less than 20° C., especially preferably less than 10° C. The production method according to this embodiment increases the production yield of the facial isomer by using the fact that the temperature at which the facial isomer is higher than the reaction temperature at which the meridional isomer is generated. Thus, it is preferable that in an initial state of a reaction that starts at the time of mixing two reaction substrates, the temperature of the mixture be set at a higher temperature. Specifically, in the step (2), the temperature of the mixture (reaction solution when a solvent is used) when reaction substrates are mixed is preferably 105° C. or higher. The temperature of the mixture is more preferably 155° C. or higher, especially preferably 180° C. or higher.

The production method according to this embodiment is usually carried out at a normal pressure, but may carried out under pressure or under a reduced pressure as necessary.

In the production method according to this embodiment, besides the aforementioned reaction substrates, a base such as an inorganic base containing an alkali metal (for example, potassium carbonate, sodium carbonate, sodium hydroxide or potassium hydrogen carbonate) or an organic amine (for example, diethylamine, triethylamine, triisobutylamine or triethanolamine) may be added for promoting the reaction.

In the production method according to this embodiment, besides the aforementioned reaction substrates, a silver compound such as $AgCF_3SO_3$, $AgCF_3COO$, $AgClO_4$, $AgBF_4$, $AgBPh_4$ or $AgPF_6$ may be added for promoting the reaction.

In the production method according to this embodiment, the used amount of a bidentate organic ligand represented by general formula (chemical formula 5) is not particularly limited as long as it is equal to or more than a stoichiometric ratio with respect to a complex of orthometallated iridium represented by general formula (chemical formula 4), but the used amount of the bidentate organic ligand is preferably 1 to 100 equivalents. When the complex of orthometallated iridium represented by general formula (chemical formula 4) is a compound represented by general formula (chemical formula 7), the used amount of the bidentate organic ligand is more preferably 2 to 100 equivalents, especially preferably 5 to 80 equivalents, particularly preferably 10 to 70 equivalents. When the complex of orthometallated iridium represented by general formula (chemical formula 4) is a compound represented by general formula (chemical formula 8), the used amount of the bidentate organic ligand is more preferably 1 to 30 equivalents, especially preferably 1 to 10 equivalents, particularly preferably 1 to 5 equivalents. When the complex of orthometallated iridium represented by general formula (chemical formula 4) is a compound represented by general formula (chemical formula 9), the used amount of the bidentate organic ligand is more preferably 1 to 30 equivalents, especially preferably 1 to 10 equivalents, particularly preferably 1 to 5 equivalents.

The method for preliminary heating in the step (1) is not particularly limited, and is, for example, a conventional external heating system such as an oil bath, a mantle heater, a block heater or a heat medium circulating jacket, or a microwave irradiation system. Among them, the microwave irradiation system is preferable because the temperature can be elevated in a shorter time.

The output of the microwave is preferably in a range of 0.2 kW to 100 kW per liter of reaction solution, more preferably in a range of 0.5 kW to 50 kW per liter of reaction solution, especially preferably in a range of 2 kW to 20 kW per liter of reaction solution.

The method for stirring the reaction solution is not particularly limited, but for example, a method of stirring by passing an inert gas, or a method using a magnetic stirrer, a stirring blade or the like is suitably used.

The complex of tris-orthometallated iridium obtained by the production method according to this embodiment has geometrical isomers, i.e. the facial isomer and the meridional isomer, and the production yields thereof can be analyzed using proton nuclear magnetic resonance (proton NMR), high performance liquid chromatography (HPLC) or the like.

The method for irradiation of a microwave is a single mode or a multi mode. In the production method according to this embodiment, either of the modes can be used, but the multi mode is more desirable.

The valence number of iridium of an iridium raw material used in the production method according to this embodiment and a complex of tris-orthometallated iridium as a product is preferably three.

For the microwave irradiation apparatus used in the production method according to this embodiment, any commercially available or previously known product can be used. The reaction is preferably carried out with a cooling pipe attached on the top of the microwave irradiation apparatus.

The material of a reaction vessel used in the production method according to this embodiment is not particularly limited, and examples thereof include borosilicate glass, quartz glass and polytetrafluoroethylene (for example, Teflon (registered trademark)).

The complexes of tris-orthometallated iridium represented by general formulae (chemical formula 4) and (chemical formula 7) to (chemical formula 9) can be produced by a known method. The known method is, for example, the method described in JP-A No. 2002-105055, Japanese Patent Application National Publication No. 2008-505076 or WO 2009/073246.

The reason why the facial isomer, which has particularly high light emission efficiency among complexes of tris-orthometallated iridium, is obtained at a good purity as compared to a case where the conventional production method is used is not clear, but the present inventors believe that the probability of generation of the facial isomer, which is advantageous in terms of thermal equilibrium, is increased by carrying out a reaction of a complex of orthometallated iridium represented by general formula (chemical formula 4) and a bidentate organic ligand represented by general formula (chemical formula 5) with the two reaction substrates mixed together after preliminarily heating at least one reaction substrate. On the other hand, it is considered that when the conventional production method (method of mixing two reaction substrates: a complex of orthometallated iridium as an iridium raw material and a bidentate organic ligand, followed by reacting the mixture under heating) is used, the meridional isomer, which is advantageous in terms of kinetics, is easily generated.

The production method according to this embodiment has a high practical value when a microwave irradiation method is employed as heating means. When production is scaled up with a microwave irradiation method used as heating means, the temperature elevation rate of the reaction solution is low, so that it takes a long time for a desired reaction temperature to be reached as compared to production before being scaled up if the microwave output is unchanged. In the case of production of a complex of tris-orthometallated iridium, the meridional isomer is more easily generated than the facial isomer at a low reaction temperature, and the meridional isomer may be easily generated when production is scaled up. Thus, for keeping the temperature elevation rate same as that before production is scaled up, it is necessary to increase irradiation energy of a microwave in accordance with the amount of a reaction liquid, but the output of a microwave generator cannot be infinitely increased, and there arises a disadvantage in terms of production costs. In the production method of the present disclosure, at least one reaction substrate is preliminarily heated, and thereafter the two reaction substrates are mixed and reacted, so that the temperature can be quickly elevated to a desired reaction temperature, thus making it possible to improve the selectivity of the facial isomer.

Examples of the complex of tris-orthometallated iridium represented by general formula (chemical formula 6) produced by the production method according to this embodiment are shown in (T-1) to (T-16) of chemical formula (chemical formula 11), but the present disclosure is not limited thereto.

[Chemical Formula 11]

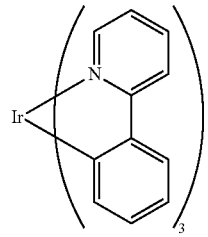

(T-1)

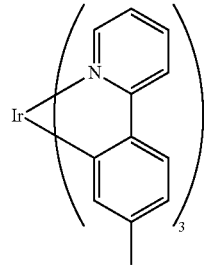

(T-2)

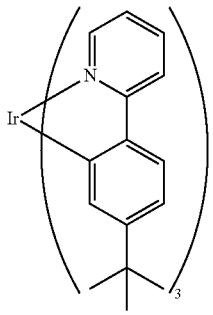

(T-3)

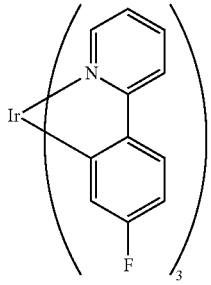

(T-4)

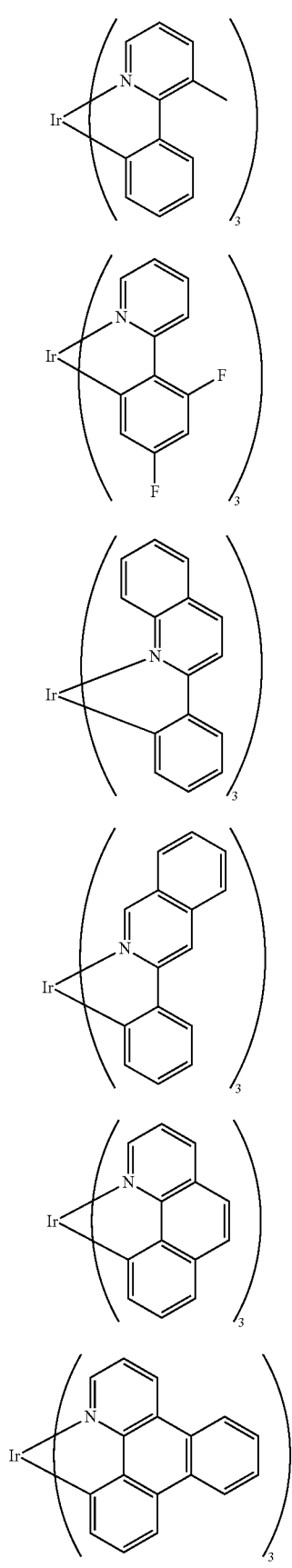
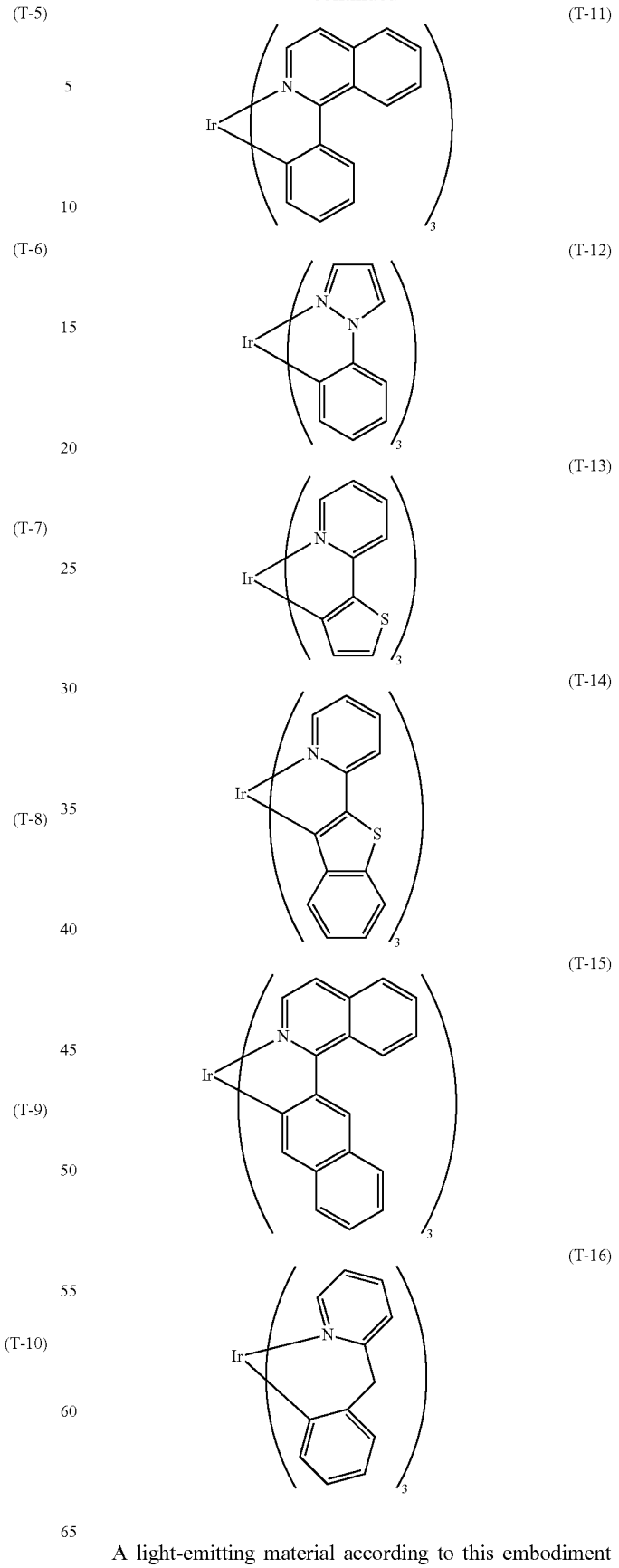
A light-emitting material according to this embodiment includes the complex of tris-orthometallated iridium produced by the production method according to this embodiment. The light-emitting material is suitable as, for example, a material of a light-emitting layer of an organic electroluminescence device.

A light-emitting device according to this embodiment uses the light-emitting material according to this embodiment. The organic electroluminescence device usually has a structure in which an anode, a hole transport layer, a light-emitting layer, an electron transport layer and a cathode are stacked in order on a substrate formed of a glass plate, a plastic plate or the like. The method for forming the light-emitting layer is not particularly limited, and can be formed by a well-known method such as a vapor deposition method or a wet deposition method. By including in a light-emitting layer of a light-emitting device a complex of tris-orthometallated iridium produced by the production method according to this embodiment, a light-emitting device excellent in light emission efficiency and durability as compared to the conventional light-emitting device can be provided. Thus, the light-emitting device according to this embodiment can be applied to, for example, OA computers, flat panel displays of wall-mounted televisions, vehicle-mounted display devices, cellular phone displays, copiers, liquid crystal displays, light sources that make use of the feature as a plane light emitter, such as backlight light sources of measuring instruments, display boards and marker lamps.

EXAMPLES

Next, the present disclosure will be described further in detail by referring to Examples, but the present disclosure is not construed as being limited to Examples.

Example 1

Production of Complex of Tris-orthometallated Iridium (T-9)

1.15 g of benzo[h]quinoline and 50 mL of special-grade ethylene glycol were placed in a 100 mL two-necked flask, an argon gas was blown into the reaction solution for 20 minutes, and thereafter the reaction solution was preliminarily heated by elevating the temperature to 210° C. (oil bath temperature) for 30 minutes using an oil bath while the reaction solution was magnetically stirred. Then, 0.495 g of a chlorine-bridged iridium dimer (D-9) was added to the reaction solution in the form of a powder, and the resulting mixture was heated to reflux at 210° C. (oil bath temperature) for 1.5 hours under an argon atmosphere. The reaction solution was cooled to room temperature, and thereafter the reaction solution was filtered to obtain a yellow solid. The yellow solid was washed with methanol, pure water and methanol again, and thereafter dried in a vacuum to obtain a complex of tris-orthometallated iridium (T-9) described in chemical formula (chemical formula 11) (yield amount: 0.584 g; yield: 94%). The product was analyzed by proton NMR (manufactured by JEOL Ltd.; JNM-ECX400: 400 MHz; in DMSO-$d_6$), and resultantly found to be a mixture of a facial isomer and a meridional isomer at a ratio of 88:12 (molar ratio). The reaction scheme is shown in reaction formula (chemical formula 12).

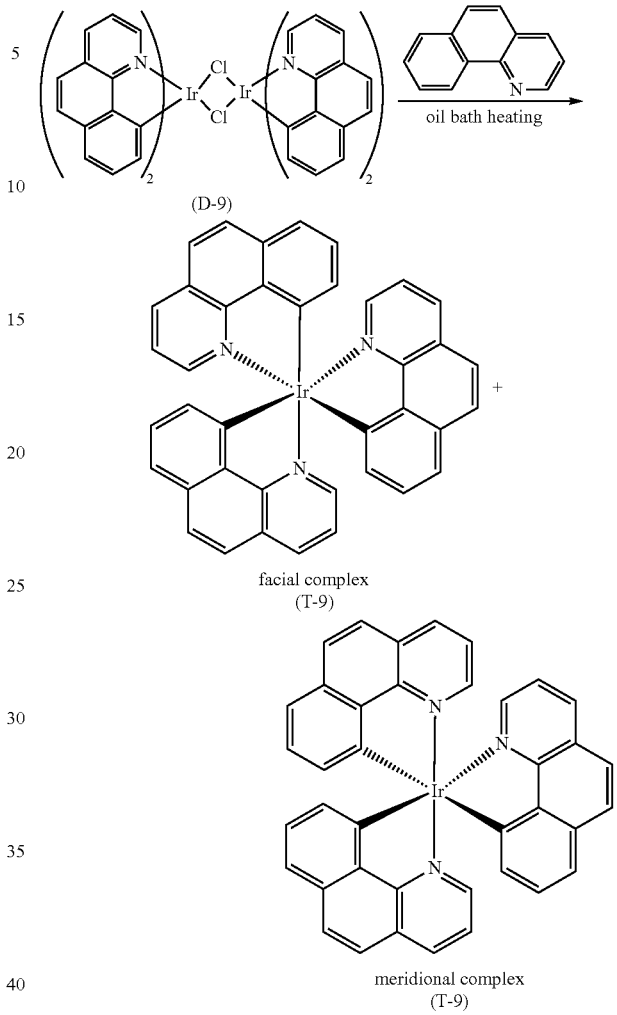

[Chemical Formula 12]

Comparative Example 1

Production of Complex of Tris-orthometallated Iridium (T-9)

1.15 g of benzo[h]quinoline, 0.50 g of a chlorine-bridged iridium dimer (D-9) and 50 mL of special-grade ethylene glycol were placed in a 100 mL two-necked flask, an argon gas was blown into the reaction solution for 20 minutes, the temperature was thereafter elevated to 210° C. (oil bath temperature) for 30 minutes using an oil bath while the reaction solution was magnetically stirred, and the reaction solution was heated to reflux at 210° C. (oil bath temperature) for 1.5 hours under an argon atmosphere. The reaction solution was cooled to room temperature, and thereafter the reaction solution was filtered to obtain a yellow solid. The yellow solid was washed with methanol, pure water and methanol again, and thereafter dried in a vacuum to obtain a complex of tris-orthometallated iridium (T-9) described in chemical formula (chemical formula 11) (yield amount: 0.561 g; yield: 90%). The product was analyzed by proton NMR (manufactured by JEOL Ltd.; JNM-ECX400: 400 MHz; in DMSO-$d_6$), and resultantly found to be a mixture of a facial isomer and a meridional isomer at a ratio of 80:20 (molar ratio).

Example 2

Production of Complex of Tris-orthometallated Iridium (T-9)

13.7 g of benzo[h]quinoline and 240 mL of special-grade ethylene glycol were placed in a 500 mL two-necked flask, and the flask was set in a microwave reaction apparatus (Microsynth manufactured by Milestone General K.K.). An argon gas was blown into the reaction solution for 25 minutes, the reaction solution was thereafter irradiated with a microwave (2450 MHz) at 1 kW while the reaction solution was magnetically stirred, and the reaction solution was preliminarily heated by elevating the temperature from room temperature to a boiling state (around 198° C. to 200° C.) in about 3 minutes. Here, irradiation of the microwave was discontinued on a temporary basis, 2.99 g of a chlorine-bridged iridium dimer (D-9) was added to the reaction solution in the form of a powder, and the resulting mixture was further irradiated with a microwave at 1 kW for 20 minutes under an argon atmosphere, and reacted at around 198° C. to 200° C. The reaction solution was cooled to room temperature, and thereafter the reaction solution was filtered to obtain a yellow solid. The yellow solid was washed with methanol, pure water and methanol again, and thereafter dried in a vacuum to obtain a complex of tris-orthometallated iridium (T-9) described in chemical formula (chemical formula 11) (yield amount: 3.54 g; yield: 95%). The product was analyzed by proton NMR (manufactured by JEOL Ltd.; JNM-ECX400: 400 MHz; in DMSO-$d_6$), and resultantly found to be a mixture of a facial isomer and a meridional isomer at a ratio of 81:19 (molar ratio). The reaction scheme is shown in reaction formula (chemical formula 13).

[Chemical Formula 13]

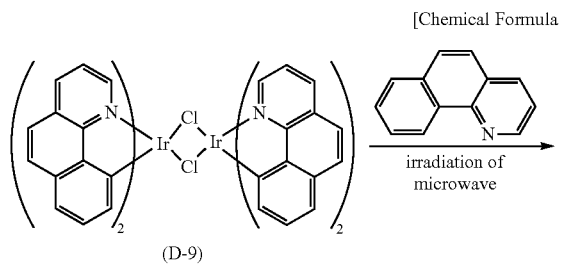

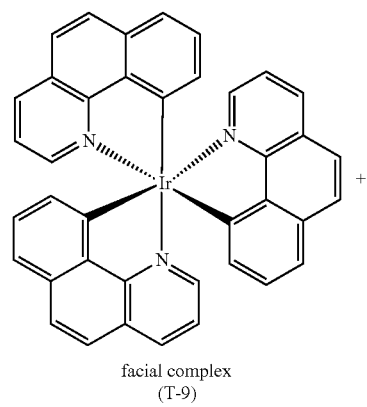

facial complex
(T-9)

+

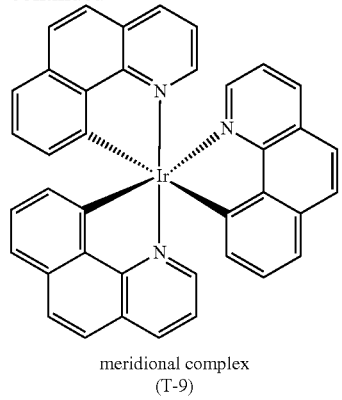

meridional complex
(T-9)

Comparative Example 2

Production of Complex of Tris-orthometallated Iridium (T-9)

14.3 g of benzo[h]quinoline, 2.99 g of a chlorine-bridged iridium dimer (D-9) and 240 mL of special-grade ethylene glycol were placed in a 500 mL two-necked flask, and the flask was set in a microwave reaction apparatus (Microsynth manufactured by Milestone General K.K.). An argon gas was blown into the reaction solution for 25 minutes, the reaction solution was thereafter irradiated with a microwave (2450 MHz) at 1 kW while the reaction solution was magnetically stirred, the temperature was elevated from room temperature to a boiling state (around 198° C. to 200° C.) in about 3 minutes, and the reaction solution was further irradiated with a microwave at 1 kW for 20 minutes under an argon atmosphere, and reacted at around 198° C. to 200° C. The reaction solution was cooled to room temperature, and thereafter the reaction solution was filtered to obtain a yellow solid. The yellow solid was washed with methanol, pure water and methanol again, and thereafter dried in a vacuum to obtain a complex of tris-orthometallated iridium (T-9) described in chemical formula (chemical formula 11) (yield amount: 3.48 g; yield: 94%). The product was analyzed by proton NMR (manufactured by JEOL Ltd.; JNM-ECX400: 400 MHz; in DMSO-$d_6$), and resultantly found to be a mixture of a facial isomer and a meridional isomer at a ratio of 66:34 (molar ratio).

Example 3

Production of Complex of Tris-orthometallated Iridium (T-9)

2.34 g of benzo[h]quinoline and 50 mL of special-grade ethylene glycol were placed in a 100 mL two-necked flask, an argon gas was blown into the reaction solution for 25 minutes, and thereafter the reaction solution was preliminarily heated by elevating the temperature to 210° C. (oil bath temperature) for 30 minutes using an oil bath while the reaction solution was magnetically stirred. Here, 0.663 g of an iridium complex (A-9) was added to the reaction solution in the form of a powder, and the resulting mixture was heated to reflux at 210° C. (oil bath temperature) for 30 minutes under an argon atmosphere. The reaction solution was cooled to room temperature, and thereafter the reaction solution was filtered to obtain a yellow solid. The yellow solid was washed with methanol, pure water and methanol again, and thereafter dried in a vacuum to obtain a complex of tris-orthometallated iridium (T-9) described in chemical formula (chemical formula 11) (yield amount: 0.575 g; yield: 93%). The product was analyzed by proton NMR (manufactured by JEOL Ltd.; JNM-ECX400: 400 MHz; in DMSO-$d_6$), and resultantly found to be a mixture of a facial isomer and a meridional isomer at a ratio of 15:85 (molar ratio). The reaction scheme is shown in reaction formula (chemical formula 14).

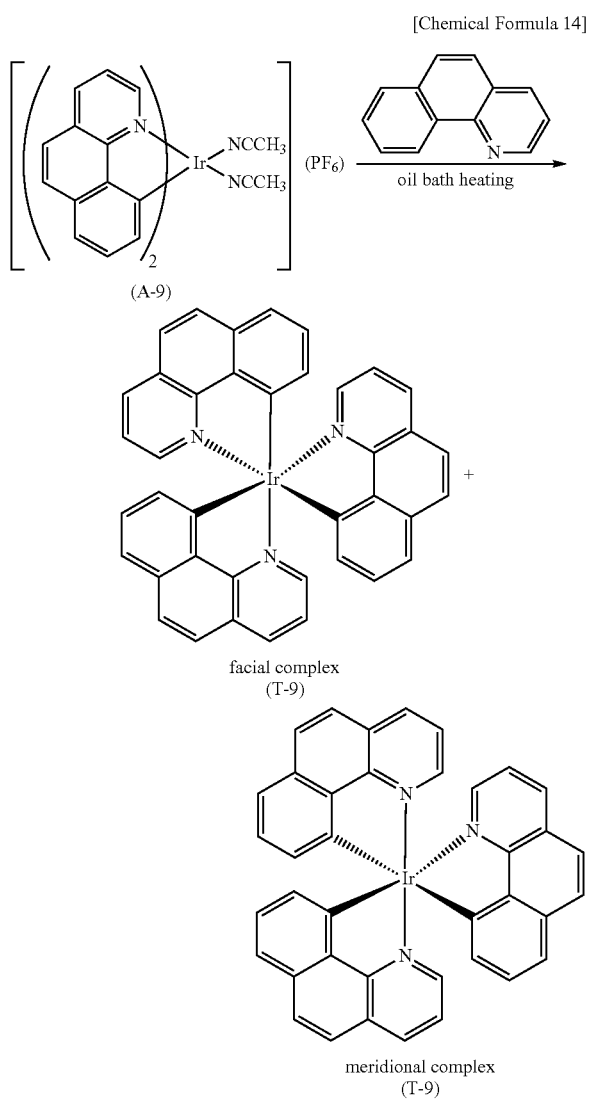

Comparative Example 3

Production of Complex of Tris-orthometallated Iridium (T-9)

2.30 g of benzo[h]quinoline, 0.665 g of an iridium complex (A-9) and 50 mL of special-grade ethylene glycol were placed in a 100 mL two-necked flask, an argon gas was blown into the reaction solution for 25 minutes, the temperature was thereafter elevated to 210° C. (oil bath temperature) for 1.5 hours using an oil bath while the reaction solution was magnetically stirred, and the reaction solution was heated to reflux at 210° C. (oil bath temperature) for 30 minutes under an argon atmosphere. The reaction solution was cooled to room temperature, and thereafter the reaction solution was filtered to obtain a yellow solid. The yellow solid was washed with methanol, pure water and methanol again, and thereafter dried in a vacuum to obtain a complex of tris-orthometallated iridium (T-9) described in chemical formula (chemical formula 11) (yield amount: 0.587 g; yield: 94%). The product was analyzed by proton NMR (manufactured by JEOL Ltd.; JNM-ECX400: 400 MHz; in DMSO-$d_6$), and resultantly found to be a mixture of a facial isomer and a meridional isomer at a ratio of 9:91 (molar ratio).

Example 4

Production of Complex of Tris-orthometallated Iridium (T-1)

300 g of 2-phenylpyridinato and 3 L of special-grade ethylene glycol were placed in a 6 L separable flask, an argon gas was blown into the reaction solution for 25 minutes, the reaction solution was irradiated with a microwave (2450 MHz) at 6 kW by a cavity-type microwave irradiation apparatus (SMW-124 manufactured by Shikoku Instrumentation CO., Inc.) while the reaction solution was stirred, and the temperature was elevated from room temperature to a boiling state (around 198° C. to 200° C.) in about 6 minutes. Here, irradiation of the microwave was discontinued on a temporary basis, 30.4 g of a chlorine-bridged iridium dimer (D-1) was added to the reaction solution in the form of a powder, and the resulting mixture was further irradiated with a microwave at 6 kW for an hour under an argon atmosphere, and reacted at around 198° C. to 200° C. The reaction solution was cooled to room temperature, and thereafter the reaction solution was filtered to obtain a yellow solid. The yellow solid was washed with methanol, pure water and methanol again, thereafter dried in a vacuum, and recrystallized from a mixed solvent of DMF and methanol to obtain a complex of tris-orthometallated iridium (T-1) described in chemical formula (chemical formula 11) (yield amount: 33.5 g; yield: 90.0%). The product was analyzed by HPLC (Prominence manufactured by Shimadzu Corporation; detected wavelength: 300 nm), and resultantly found to be a mixture of a facial isomer and a meridional isomer at a ratio of 99.8:0.2 (molar ratio). The reaction scheme is shown in reaction formula (chemical formula 15).

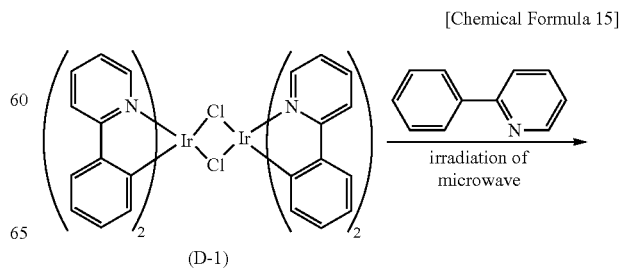

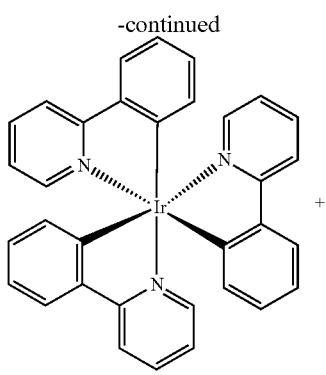

facial complex
(T-1)

+

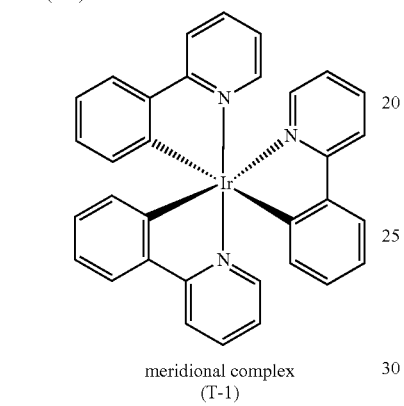

meridional complex
(T-1)

Comparative Example 4

Production of Complex of Tris-orthometallated Iridium (T-1)

300 g of 2-phenylpyridinato, 30.1 g of a chlorine-bridged iridium dimer (D-1) and 3 L of special-grade ethylene glycol were placed in a 6 L separable flask, and the flask was set in a cavity-type microwave irradiation apparatus (SMW-124 manufactured by Shikoku Instrumentation CO., Inc.). An argon gas was blown into the reaction solution for 30 minutes, the reaction solution was thereafter irradiated with a microwave (2450 MHz) at 6 kW while the reaction solution was magnetically stirred, the temperature was elevated from room temperature to a boiling state (around 198° C. to 200° C.) in about 6 minutes, and the reaction solution was further irradiated with a microwave at 6 kW for an hour under an argon atmosphere, and reacted at around 198° C. to 200° C. The reaction solution was cooled to room temperature, and thereafter the reaction solution was filtered to obtain a yellow solid. The yellow solid was washed with methanol, pure water and methanol again, thereafter dried in a vacuum, and recrystallized from a mixed solvent of DMF and methanol to obtain a complex of tris-orthometallated iridium (T-1) described in chemical formula (chemical formula 11) (yield amount: 33.5 g; yield: 90.4%). The product was analyzed by HPLC (Prominence manufactured by Shimadzu Corporation; detected wavelength: 300 nm), and resultantly found to be a mixture of a facial isomer and a meridional isomer at a ratio of 99.2:0.8 (molar ratio).

Example 5

Production of Complex of Tris-orthometallated Iridium (T-6)

3.93 g of 2-(2,4-difluorophenyl) pyridine and 50 mL of special-grade ethylene glycol were placed in a 100 mL two-necked flask, an argon gas was blown into the reaction solution for 20 minutes, and thereafter the reaction solution was preliminarily heated by elevating the temperature to 210° C. (oil bath temperature) for 50 minutes using an oil bath while the reaction solution was magnetically stirred. Then, 0.499 g of a chlorine-bridged iridium dimer (D-6) was added to the reaction solution in the form of a powder, and the resulting mixture was heated to reflux at 210° C. (oil bath temperature) for 1.5 hours under an argon atmosphere. The reaction solution was cooled to room temperature, and thereafter the reaction solution was filtered to obtain a light-yellow solid. The light-yellow solid was washed with methanol, pure water and methanol again, and thereafter dried in a vacuum to obtain a complex of tris-orthometallated iridium (T-6) described in chemical formula (chemical formula 11) (yield amount: 0.584 g; yield: 93%). The product was analyzed by proton NMR (manufactured by JEOL Ltd.; JNM-ECX400: 400 MHz; in $CDCl_3$), and resultantly found to be a mixture of a facial isomer and a meridional isomer at a ratio of 82:18 (molar ratio). The reaction scheme is shown in reaction formula (chemical formula 16).

[Chemical Formula 16]

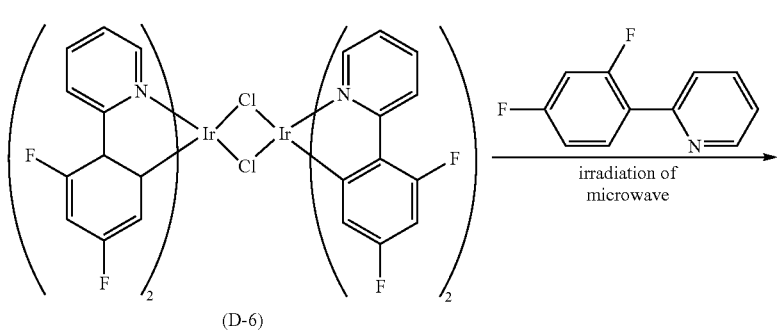

(D-6)

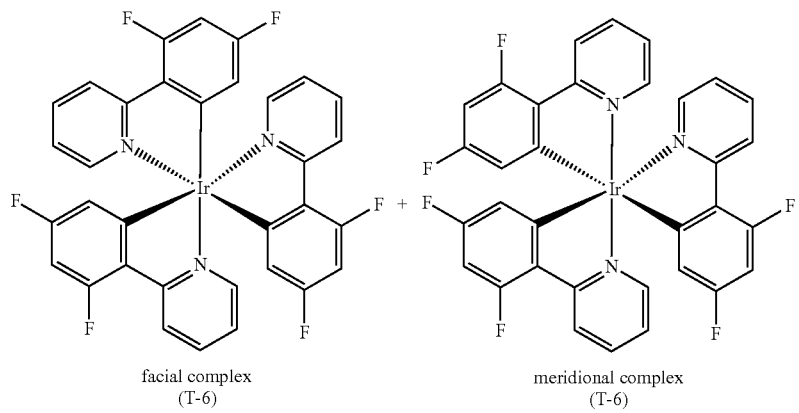

facial complex (T-6)     meridional complex (T-6)

Comparative Example 5

Production of Complex of Tris-orthometallated Iridium (T-6)

3.93 g of 2-(2,4-difluorophenyl) pyridine, 0.500 g of a chlorine-bridged iridium dimer (D-6) and 50 mL of special-grade ethylene glycol were placed in a 100 mL two-necked flask, an argon gas was blown into the reaction solution for 20 minutes, the temperature was thereafter elevated to 210° C. (oil bath temperature) for 50 minutes using an oil bath while the reaction solution was magnetically stirred, and the reaction solution was heated to reflux at 210° C. (oil bath temperature) for 1.5 hours under an argon atmosphere. The reaction solution was cooled to room temperature, and thereafter the reaction solution was filtered to obtain a light-yellow solid. The light-yellow solid was washed with methanol, pure water and methanol again, and thereafter dried in a vacuum to obtain a complex of tris-orthometallated iridium (T-6) described in chemical formula (chemical formula 11) (yield amount: 0.582 g; yield: 93%). The product was analyzed by proton NMR (manufactured by JEOL Ltd.; JNM-ECX400: 400 MHz; in CDCl$_3$), and resultantly found to be a mixture of a facial isomer and a meridional isomer at a ratio of 76:24 (molar ratio).

Example 6

Production of Complex of Tris-orthometallated Iridium (T-3)

5.00 g of 2-(4-tert-butylphenyl)pyridine and 50 mL of special-grade ethylene glycol were placed in a 100 mL two-necked flask, an argon gas was blown into the reaction solution for 20 minutes, and thereafter the reaction solution was preliminarily heated by elevating the temperature to 210° C. (oil bath temperature) for an hour using an oil bath while the reaction solution was magnetically stirred. Then, 0.500 g of a chlorine-bridged iridium dimer (D-3) was added to the reaction solution in the form of a powder, and the resulting mixture was heated to reflux at 210° C. (oil bath temperature) for an hour under an argon atmosphere. The reaction solution was cooled to room temperature, and thereafter the reaction solution was filtered to obtain a yellow solid. The yellow solid was washed with methanol, pure water and methanol again, and thereafter dried in a vacuum to obtain a complex of tris-orthometallated iridium (T-3) described in chemical formula (chemical formula 11) (yield amount: 0.453 g; yield: 71%). The product was analyzed by proton NMR (manufactured by JEOL Ltd.; JNM-ECX400: 400 MHz; in CDCl$_3$), and resultantly found that the ratio of a facial isomer and a meridional isomer was 100:0 (molar ratio). The reaction scheme is shown in reaction formula (chemical formula 17).

[Chemical Formula 17]

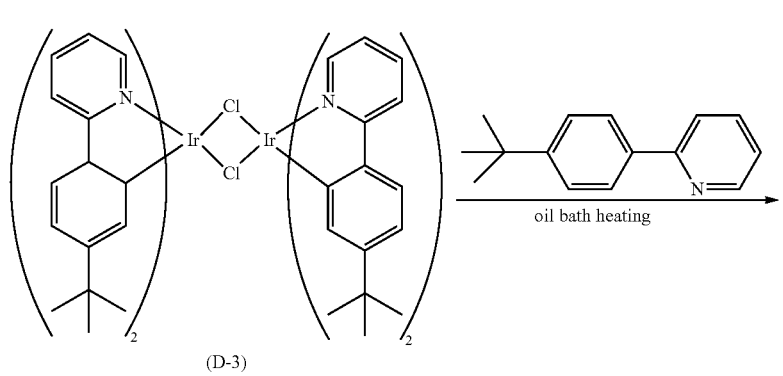

(D-3)

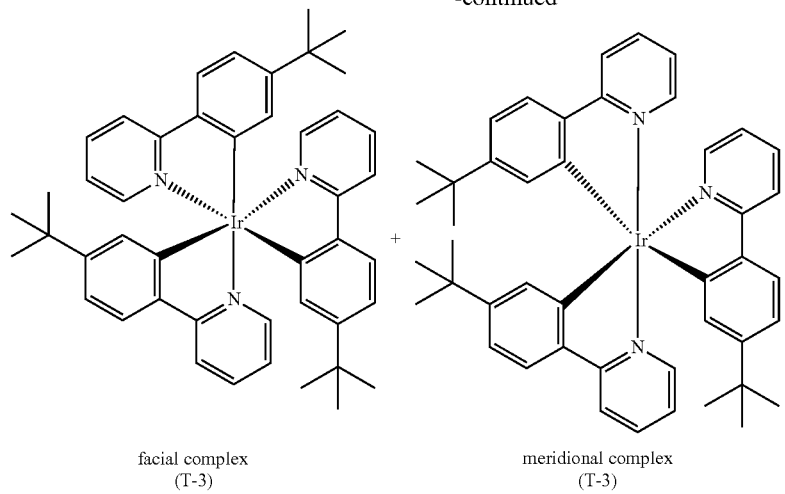

facial complex
(T-3)

meridional complex
(T-3)

Comparative Example 6

Production of Complex of Tris-orthometallated Iridium (T-3)

5.00 g of 2-(4-tert-butylphenyl) pyridine, 0.500 g of a chlorine-bridged iridium dimer (D-3) and 50 mL of special-grade ethylene glycol were placed in a 100 mL two-necked flask, an argon gas was blown into the reaction solution for 20 minutes, the temperature was thereafter elevated to 210° C. (oil bath temperature) for an hour using an oil bath while the reaction solution was magnetically stirred, and the reaction solution was heated to reflux at 210° C. (oil bath temperature) for an hour under an argon atmosphere. The reaction solution was cooled to room temperature, and thereafter the reaction solution was filtered to obtain a yellow solid. The yellow solid was washed with methanol, pure water and methanol again, and thereafter dried in a vacuum to obtain a complex of tris-orthometallated iridium (T-3) described in chemical formula (chemical formula 11) (yield amount: 0.422 g; yield: 67%). The product was analyzed by proton NMR (manufactured by JEOL Ltd.; JNM-ECX400: 400 MHz; in CDCl$_3$), and resultantly found that the ratio of a facial isomer and a meridional isomer was 100:0 (molar ratio).

From Examples described above, it has been revealed that in the production method according to the present disclosure (Examples 1 to 5), generation of the meridional isomer is suppressed and the purity of the facial isomer is improved as compared to the conventional production method (Comparative Examples 1 to 5). As it has been revealed that the facial isomer of tris-orthometallated iridium is superior in light emission efficiency and stability to its geometrical isomer, i.e. the meridional isomer, a light-emitting device having high efficiency and high durability can be prepared by using as a light-emitting device material a complex of tris-orthometallated iridium produced by the production method according to the present disclosure. Since reduction of the meridional isomer that is not preferable as a light-emitting device material by various purification methods (recrystallization, column chromatography, sublimation refinement, and the like.) requires considerable efforts and time, the production method according to the present disclosure can highly contribute to reduction of production costs, leading to a significant practical advantage.

The production yield of the facial isomer is 100% in both Example 6 and Comparative Example 6, but the yield of the facial isomer of the complex of tris-orthometallated iridium (value obtained by multiplying the yield of the resulting complex of tris-orthometallated iridium by the production yield of the facial isomer) is higher in Example 6 than in Comparative Example 6.

The invention claimed is:

1. A method for producing a complex of tris-orthometallated iridium in which a complex of orthometallated iridium represented by general formula (chemical formula 47) and a bidentate organic ligand represented by at least one of (7) to (15) in general formula (chemical formula 10) are reacted as reaction substrates to produce a complex of tris-orthometallated iridium represented by general formula (chemical formula 6), wherein the method comprises, in order,
a step (1) of preliminarily heating the bidentate organic ligand;
a step (2) of mixing the complex of orthometallated iridium and the bidentate organic ligand; and
a step (3) of reacting the complex of orthometallated iridium and the bidentate organic ligand, the step (3) being carried out under irradiation of a microwave;

[Chemical Formula 7]

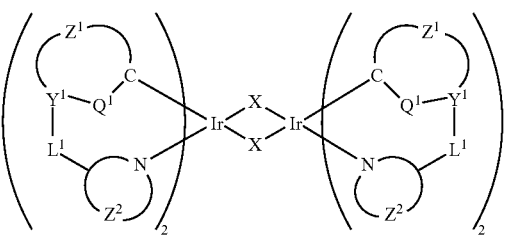

wherein, in general formula (chemical formula 7), X represents a halogen atom; $Z^1$ represents a group of non-metal atoms required for forming a benzene ring or a naphthalene ring; $Z^2$ represents a group of non-metal atoms required for forming a pyridine ring; wherein the ring formed may form a fused ring with still another ring; $L^1$ represents a single bond;

$Y^1$ represents a carbon atom; when $Y^1$ is a carbon atom, $Q^1$ indicates that a carbon atom and $Y^1$ are bonded to each other by a double bond;
[Chemical Formula 10]
(7)
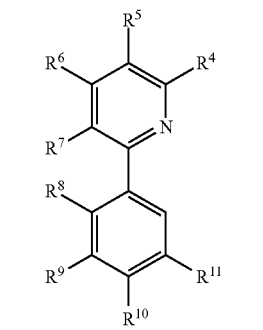
(8)
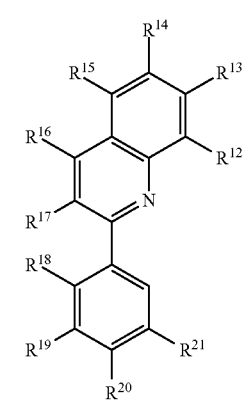
(9)
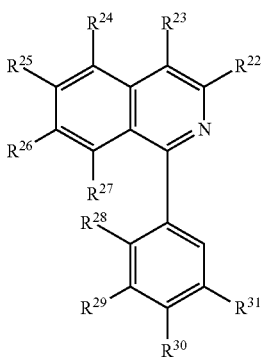
(10)
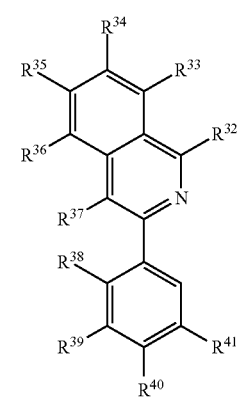
-continued
(11)
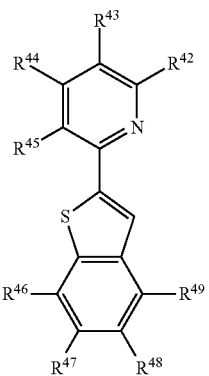
(12)
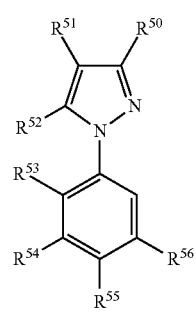
(13)
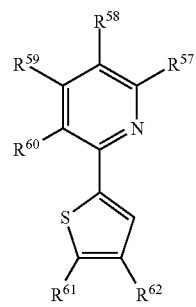
(14)
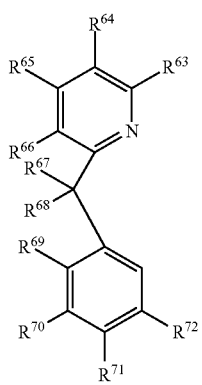

(15) 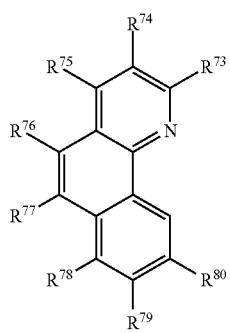

(16) 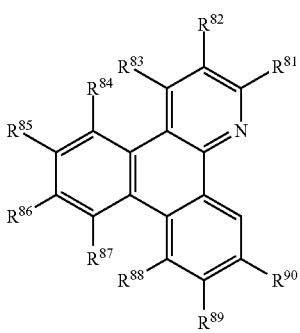

(17) 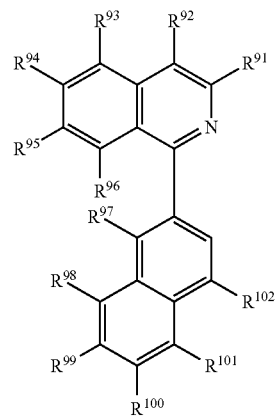

wherein in (7) to (17) shown in general formula (chemical formula 10), $R^4$ to $R^{102}$ each represent a hydrogen atom, a deuterium atom, an alkyl group, an alkenyl group, an alkynyl group, an aryl group, an amino group, an alkoxy group, an aryloxy group, a heterocyclic-oxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heterocyclic-thio group, a sulfonyl group, a sulfinyl group, a ureide group, a phosphoric amide group, a hydroxy group, a mercapto group, a halogen atom, a cyano group, a sulfo group, a carboxyl group, a nitro group, a trifluoromethyl group, a hydroxamic acid group, a sulfino group, a hydrazino group, an imino group, a heterocyclic group, a silyl group, or a silyloxy group;

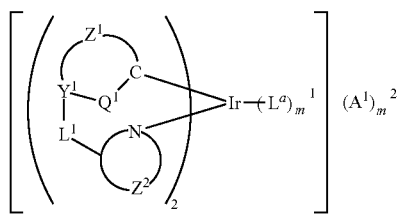

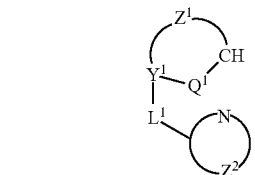

[Chemical Formula 6]

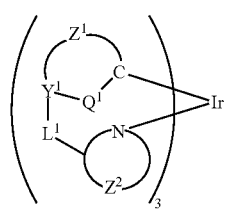

wherein in general formula (chemical formula 6), $Z^1$ represents a group of non-metal atoms required for forming a benzene ring or a naphthalene ring; $Z^2$ represents a group of non-metal atoms required for forming a pyridine ring; wherein the ring formed may form a fused ring with still another ring; $L^1$ represents a single bond; $Y^1$ represents a carbon atom; when $Y^1$ is a carbon atom, $Q^1$ indicates that a carbon atom and $Y^1$ are bonded to each other by a double bond.

2. The method for producing a complex of tris-orthometallated iridium according to claim 1, wherein the reaction temperature in the step (3) is in a range of 100 to 300° C.

3. The method for producing a complex of tris-orthometallated iridium according to claim 1, wherein the preliminary heating temperature in the step (1) is equal to or lower than the reaction temperature in the step (3) and in a range of 100 to 300° C.

\* \* \* \* \*